US007964209B2

(12) United States Patent
Ranade et al.

(10) Patent No.: US 7,964,209 B2
(45) Date of Patent: Jun. 21, 2011

(54) ORIENTING POLYMER DOMAINS FOR CONTROLLED DRUG DELIVERY

(75) Inventors: Shrirang V. Ranade, Arlington, MA (US); Robert E. Richard, Wrentham, MA (US); Kinh-Luan (Lenny) D. Dao, Randolph, MA (US); Samuel P. Gido, Hadley, MA (US); Akinbode Idowu Isaacs-Sodeye, South Hadley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1211 days.

(21) Appl. No.: 11/005,852

(22) Filed: Dec. 7, 2004

(65) Prior Publication Data

US 2006/0121076 A1 Jun. 8, 2006

(51) Int. Cl.
*A61F 13/00* (2006.01)
*A61F 2/00* (2006.01)
*B05D 3/02* (2006.01)
*A61M 31/00* (2006.01)

(52) U.S. Cl. ........ 424/425; 424/422; 427/2.26; 604/500
(58) Field of Classification Search .................... 424/425
See application file for complete search history.

(56) References Cited

U.S. PATENT DOCUMENTS

| 6,545,097 B2* | 4/2003 | Pinchuk et al. ............... 525/240 |
| 2003/0235603 A1 | 12/2003 | Schwarz et al. |
| 2004/0051201 A1* | 3/2004 | Greenhalgh et al. ...... 264/172.11 |
| 2004/0058887 A1* | 3/2004 | Bowlin et al. .................. 514/44 |
| 2004/0067301 A1 | 4/2004 | Ding ............................ 427/2.25 |

(Continued)

FOREIGN PATENT DOCUMENTS

JP 2005314526 11/2005
(Continued)

OTHER PUBLICATIONS http://en.wikipedia.org/wiki/Electrospinning (Wikipedia).*
(Continued)

*Primary Examiner* — Shanon A Foley
*Assistant Examiner* — Sarah Al-Awadi
(74) *Attorney, Agent, or Firm* — Myers & Williams PC; David B. Bonham; Keum J. Park (57) ABSTRACT

The present invention provides a method for the formation of a medical device that comprises a therapeutic agent and a release region, which regulates the rate at which the therapeutic agent is released from the medical device. The method comprises providing a precursor region that comprises a polymer composition comprising two or more microphase separated polymer domains that are immiscible with one another, and forming said release region by a process that comprises applying an orienting field comprising an electric field, a magnetic field, a mechanical shear field, or a solvent gradient field, or a combination of two or more fields to said precursor region, wherein said field or combination of fields changes the spatial orientation of the microphase separated polymer domains within the release region. The electric, magnetic, mechanical shear or solvent gradient field is of sufficient strength to change the spatial orientation of the microphase separated domains. Moreover, the spatial orientation of the immiscible microphase separated polymer domains affects the rate of release of the therapeutic agent from the medical device. Hence, the present invention is further directed to methods of modulating the rate of release of a therapeutic agent from a medical device. Other aspects of the invention are directed to medical devices formed from the above techniques.

33 Claims, 6 Drawing Sheets

U.S. PATENT DOCUMENTS

2006/0184112 A1* 8/2006 Horn et al. ............... 604/103.08
2008/0018015 A1* 1/2008 McHugh et al. ......... 264/211.16

FOREIGN PATENT DOCUMENTS

WO     WO 02/076523 A2    10/2002
WO     WO 2006/047490 A2    5/2006

OTHER PUBLICATIONS

Jeffrey Pyun et al., "Synthesis of Nanocomposite Organic/Inorganic Hybrid Materials Using Controlled/"Living" Radical Polymerization," *Chem. Mater.*, vol. 13, 2001, pp. 3436-3448.

Yoav Tsori et al., "Structural Changes in Block Copolymers: Coupling of Electric Field and Mobile Ions," *Physical Review Letters*, vol. 90, No. 14, Apr. 11, 2003, pp. 145504-1-145504-4.

Yoav Tsori et al., "Thin Film Diblock Copolymers in Electric Field: Transition from Perpendicular to Parallel Lamellae," *Macromolecules*, vol. 35, 2002, pp. 5161-5170.

T. Thurn-Albrecht et al., "Overcoming Interfacial Interactions with Electric Fields," *Macromolecules*, vol. 33, 2000, pp. 3250-3253.

Figure: ma991896zf00001. Http://pubs.acs.org/isubscribe/journals/mamobx/33/i09/figures/ma991896zf00001.html. Jul. 18, 2003 download.

Tsori, Y. et al., "Diblock copolymer ordering induced by patterned surfaces," Europhsyics Letters, 53 (6), Mar. 15, 2001, pp. 722-728.

Tsori, Y, et al., "Ordering Mechanisms in Confined Diblock Copolymers," Interface Science 11, 2003, pp. 259-268.

Tsori, Y. et al., "Ordered Morphologies of Confined Diblock Copolymers," Mat. Res. Soc. Symp. Proc. vol. 651, pp. T8.1.1-T8.1.11, 2001.

Tsori, Y. et al., Diblock copolymer thin films: Parallel and perpendicular lamellar phases in the week segregation limit, The European Physical Journal E 5, pp. 605-614, 2001.

Tsori, Y., et al., "Thin Film Diblock Copolymers in Electric Field: Transition from Perpendicular to Parallel Lamellae," Macromolecules 2002, 35, published May 18, 2002, pp. 5161-5170.

Tsori, Y. et al., Structural Changes in Block Copolymers: Coupling of Electric Field and Mobile Ions, Physical Review Letters, vol. 90, No. 14, Apr. 11, 2003, pp. 145504-1-145504-4.

Böltau, Martin et al., "Surface-induced structure formation of polymer blends on patterned substrates," Nature, vol. 391, Feb. 1998, pp. 877-879.

Elhadj, S., et al., "Orientation of self-assembled block copolymer cylinders perpendicular to electric field in mesoscale film," Applied Physics Letters, vol. 82, No. 6, Feb. 10, 2003, pp. 871-873.

* cited by examiner

ORIENTING POLYMER DOMAINS FOR CONTROLLED DRUG DELIVERY

FIELD OF THE INVENTION

The present invention relates to implantable or insertable medical devices for controlled delivery of one or more therapeutic agents. The present invention also relates to methods for forming a device that modulates the release of therapeutic agents from the device.

BACKGROUND OF THE INVENTION

Numerous polymer-based medical devices have been developed for the delivery of therapeutic agents to the body. The desired release profile for the therapeutic agent is dependent upon the particular treatment at hand, including the specific condition being treated or prevented, the specific site of administration, the specific therapeutic agent selected, and so forth.

In accordance with some typical delivery strategies, a therapeutic agent is provided within a polymeric carrier layer and/or beneath a polymeric barrier layer that is associated with a medical device. Once the medical device is placed at the desired location within a patient, the therapeutic agent is released from the medical device at a rate that is dependent upon the nature of the polymeric carrier and/or barrier layer.

Although controlled release of a therapeutic agent by means of polymeric materials has existed in various forms for several years, there is a continuing need for improved and more precise drug delivery systems, including polymer-containing materials, whose release characteristics may be readily modulated depending on the required need.

SUMMARY OF THE INVENTION

These and other challenges of the prior art are addressed by the present invention.

According to one aspect of the present invention, a method is provided for the formation of a medical device that comprises a therapeutic agent and a release region, which regulates the rate at which the therapeutic agent is released from the medical device. The method comprises: (a) providing a precursor region containing a polymer composition that comprises two or more immiscible polymer phases or microphase separated polymer domains that are immiscible with one another; and (b) forming the release region by a process that comprises applying a field comprising an electric field, a magnetic field, a mechanical shear field, a solvent gradient field, or a combination of two or more fields to the precursor region, wherein said field or combination of fields changes the spatial orientation of the immiscible polymer phases or the microphase separated polymer domains within the release region.

The release region comprises a polymer composition comprising two or more immiscible polymer phases or a block copolymer. The spatial orientation of the microphase separated polymer domains or immiscible polymer phases affects the rate of release of the therapeutic agent from the medical device. Hence, the present invention is also directed to methods of modulating the rate of release of a therapeutic agent from a medical device.

In certain embodiments, the precursor region comprises a solvent system in addition to the polymer composition, and the precursor region is subjected to the electric field concurrently with the removal of the solvent system from the precursor region to form the release region. In such embodiments, the removal of the solvent itself creates a directional field or concentration gradient that may also be effective in aligning microphase separated morphologies.

In certain other embodiments, the precursor region is in the form of a melt, and the precursor region is subjected to the electric and/or other field concurrently with solidification of the melt.

The release region can be, for example, a carrier region that includes the therapeutic agent, or a barrier region that is disposed over a source of therapeutic agent.

The microphase separated polymer domains can be provided, for example, by providing two or more polymers in the release region or by providing a block copolymer within the release region.

In certain embodiments, the release region comprises microphase separated polymer domains comprising a plurality of discontinuous and substantially aligned cylinders within a continuous polymer matrix. In other embodiments, the release region comprises microphase separated polymer domains comprising a plurality of alternating microphase separated lamellae. In some embodiments, lamellae of one polymer alternate with lamellae of at least one other polymer. In other embodiments, the alternating lamellae comprise a block copolymer. The cylinders or lamellae can be aligned, for example, such that they are substantially parallel with a surface of the release region, substantially perpendicular with respect to the surface, or substantially oblique with respect to the surface.

In certain beneficial embodiments, the release region is in the form of a release layer disposed over a substrate. Typical thicknesses for release regions in accordance with the present invention range from about 1 to about 50 microns.

Other aspects of the invention are directed to medical devices formed using the above techniques.

One advantage of the present invention is that implantable or insertable medical devices can be provided, from which the release of a therapeutic agent can be modulated.

Another advantage of the present invention is that the rate of release of a therapeutic agent from a particular delivery system may be readily modified, depending on the required need.

These and other embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of the embodiments. The detailed description of the embodiments which follows is intended to illustrate but not limit the invention. The scope of the invention is defined by the appended claims.

In one aspect, a method is provided for the formation of a medical device that comprises a therapeutic agent and a release region that regulates the rate at which the therapeutic agent is released from the medical device. The method comprises: (a) providing a precursor region containing a polymer composition that comprises two or more microphase separated polymer domains that are immiscible with one another; and (b) forming the release region by a process comprising applying an electric field, or other fields such as, but not limited to, mechanical shear field or solvent gradient field, laser gradient field or magnetic field to the precursor region, wherein the electric and/or other alignment-inducing field is of sufficient strength to change the spatial orientation of the microphase separated polymer domains within the release region.

Microphase separation of immiscible polymer segments due to thermodynamic interactions is well documented in the literature. Contributing factors include but are not limited to the composition and the molecular weight of the polymer blocks. A single block copolymer having two (or more) immiscible blocks can be used to create a polymer composition having two (or more) types of microphase separated polymer domains, so long as the blocks are sufficiently long to result in microphase separation.

A polymer "block," as used herein, refers to a grouping of 10 or more constitutional (monomer) units, commonly 20 or more, 50 or more, 100 or more, 200 or more, 500 or more, or even 1000 or more units. A "chain" is a linear (unbranched) grouping of 10 or more constitutional units (i.e., a linear block).

In some preferred embodiments, the microphase separated polymer domains are provided by a block copolymer such as a diblock copolymer, a triblock copolymer or a branched block copolymer (e.g., a star block copolymer, a comb block copolymer or a dendritic block copolymer).

In other embodiments, a polymer composition with two or more immiscible phases is provided by mixing or blending two or more immiscible polymers, for instance: (a) two or more immiscible homopolymers to form a two- or multi-phase polymer system (e.g., an admixture of a polystyrene homopolymer and isobutylene homopolymer), (b) one or more homopolymers and one or more copolymers, including block copolymers which form two or more microphase separated domains and also copolymers which form only a single phase (e.g., random copolymers, alternating copolymers and single-phase-forming block copolymers, which are in contrast with block copolymers having immiscible blocks that are sufficiently large to result in microphase separation), or (c) two or more copolymers, which form two or more microphase separated domains. As one specific example, it is possible to provide polymer release regions that contain (a) two microphase separated domains corresponding to immiscible blocks of sufficient length within a block copolymer and, optionally, (b) a third polymer phase corresponding to a separate immiscible homopolymer.

Where block copolymers are selected for use in the release regions of the present invention, the copolymer can be, for example, in the form of a diblock copolymer (sometimes referred to as AB-type block copolymers), a triblock copolymer (e.g., comprising a midblock and a pair of endblocks, sometimes referred to as ABA-type block copolymers), or a multi-block copolymer of the (AB)n type. There are several other types, such as ABC block copolymers containing three chemically different blocks, star block copolymers (e.g., comprising a structure having a central multifunctional junction point with three or more connecting arms, usually of the ABn type), dendritic copolymers (e.g., comprising a multiply branching structure radiating out from a central core) or a graft copolymers having a comb-like architecture (e.g., comprising a main chain block and a plurality of grafted side chain blocks), and other more complex molecular configurations.

Most block copolymers are microphase separated, that is, at least two of the blocks materials are segregated from one another to form separate domains on at least a micron or sub-micron (e.g., nanometer) length scale or larger. In their idealized forms, the three most common morphologies observed are spheres, cylinders, and lamellae. Other typical morphologies, in addition to spheres, cylinders and lamellae that are observed include the cubic bicontinuous gyroid structure, as well as hexagonally perforated lamellae. Of course, as would be appreciated by one of skill in the art, combined morphologies in which the characteristics of two or more of these common morphologies are found, such as a predominantly cylindrical morphology having some lamellar characteristics, are all within the scope of the present invention.

Figure 1:
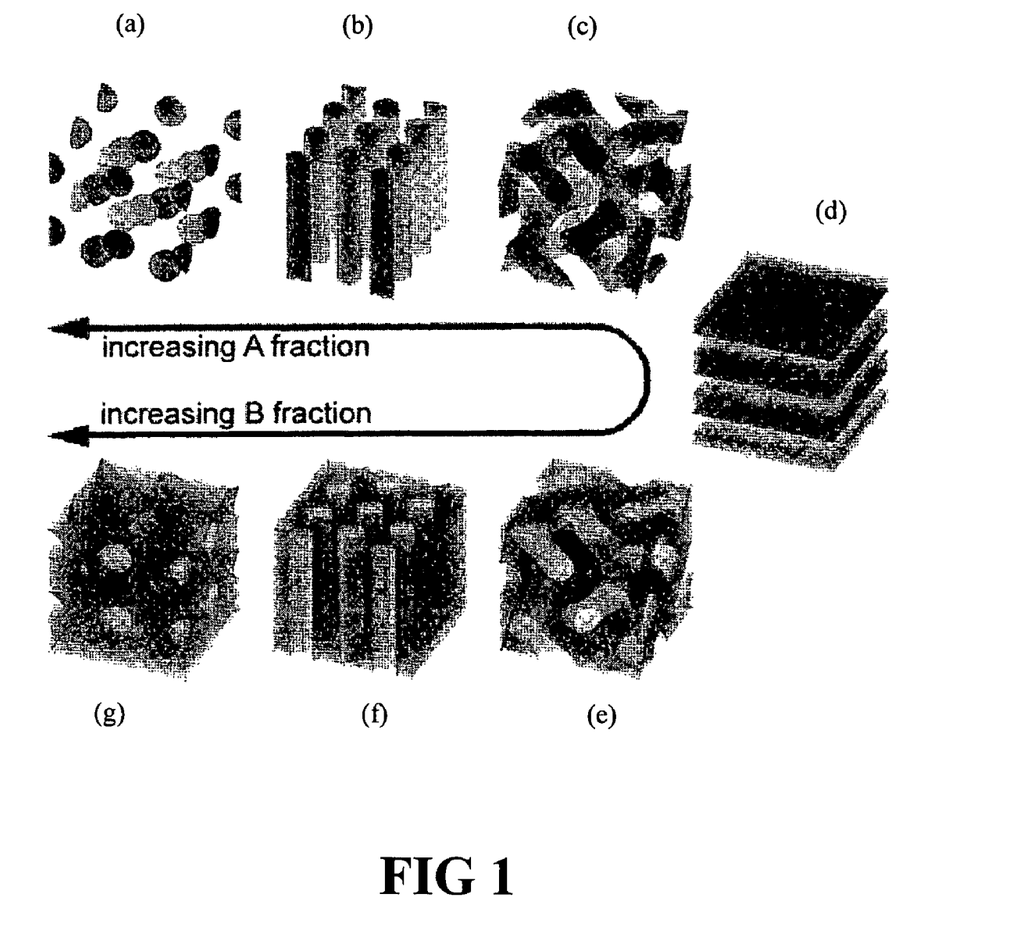
FIG. 1 schematically illustrates typical idealized morphologies of block copolymers comprising AB and ABA systems.

Some typical idealized morphologies of block copolymers comprising AB and ABA systems are illustrated below in FIG. 1. As the fraction of A goes from high to low, the morphologies typically encountered are: (a) spheres of B in a matrix of A (e.g., body centered cubic lattice), (b) cylinders of B in a matrix of A (e.g., hexagonal lattice), (c) dual labyrinths of B in a matrix of A (e.g., double gyroid), otherwise known as a bicontinuous system, (d) alternating sheets of A and B (e.g., lamellae), (e) dual labyrinths of A in a matrix of B, (f) cylinders of A in a matrix of B, and (g) spheres of A in a matrix of B.

Block copolymers are known to self-assemble into a variety of ordered structures, with a length scale ranging from nanometers to micrometers. These self-assembling, ordered morphologies have been studied for a wide variety of applications, including lithographic templates, high-density porous media, or scaffolds for nanoscopic devices. Typically, block copolymers contain asymmetrical or partially ordered microphases, for example, lamellae which may only be partially aligned along an axis. In the bulk, mechanical shear has been successfully used to align the microdomains.

Alignment of the domains of block copolymers by application of an electric field has also been attempted. For macroscopic samples, the high-voltage difference required between two bounding electrodes may become prohibitive. For thin films of block copolymers, on the other had, it has been shown that application of an electric field can change the orientation and even the structure of the immiscible phases of the block copolymers with respect to one another. That is, electric fields have been shown to orient microscopic and/or nanoscopic domains within thin copolymer film systems. For example, in a thin film comprising a lamellar block copolymer, where the lamellae are originally parallel to the confining surfaces, the application of an electric field perpendicular to the surfaces can cause the block copolymer to transform from a parallel to a perpendicular orientation with respect to the confining surfaces. Complete orientation of asymmetric diblock copolymers of polystyrene and poly(methylmethacrylate) having cylindrical microdomains has been achieved by applying a threshold electric field, according to Thurn-Albrecht et al., "Overcoming Interfacial Interactions with Electric Fields," *Macromolecules*, 33(9):3250-3253 (2000), the contents of which are hereby incorporated by reference in their entirety.

While not wishing to be bound by theory, it is believed that the critical field Ec for this transition is caused by a competition between the electric field and interfacial interactions (i.e., surface interactions). See Tsori et al., Thin Film Diblock Copolymers in Electric Field: Transition from Perpendicular to Parallel Lamellae, *Macromolecules*, 35:5161-5170 (2002), Tsori et al., Structural Changes in Block Copolymers: Coupling of Electric Field and Mobile Ions, *Physical Review Letters*, 90(14):145504-1-145504-4 (2003), the contents of which articles are hereby incorporated by reference in their entirety. A threshold field strength must typically be exceeded to fully align the morphology of the block copolymer. This threshold field strength has been found to be a function of the interfacial energies of the components comprising the copolymer, and would readily be determined for a particular polymer system by one of skill in the art. Typical electric fields range, for example, from about 5 to about 50 V/micron.

Applying these principles and techniques to the art of drug delivery systems and medical devices, the release of a therapeutic agent from a release region comprising a polymer composition that further comprises two or more microphase separated polymer domains (e.g., such as are observed for diblock or triblock copolymers, wherein, for example, blocks of a first polymer are present as spheres, cylinders, or lamellae within a continuous matrix of a second and/or third block), can be modulated by changing the alignment, ordering or otherwise altering the spatial orientation of the polymer domains.

Thus, in one aspect, the invention provides a method of orienting the polymer domains of a microphase separated composition with respect to one another by the application of an electrical field. In one embodiment of this aspect, the invention provides a method of modulating a rate of release of a therapeutic agent from a release region that constitutes at least a portion of an implantable or insertable medical device. Preferably, the release region is in the form of a thin film, with the electric field disrupting interfacial interactions at the surface of the thin film. The electric field causes at least a partial reordering (resulting, for example, in a substantially perpendicular or parallel ordering) of the microphase separated domains with respect to a surface of said release region and/or with respect to each other.

In some embodiments of the invention, the spatial orientation of two or more microphase separated domains or groups of microphase separated domains with respect to one another is modified by subjecting the release region to a mechanical shear or solvent gradient field or other field. As with the electric field above, a threshold field strength should be exceeded in order to achieve a substantial change in the spatial orientation of the domains, which threshold field strength would readily be determined for a particular polymer system by one of skill in the art.

In yet other embodiments, the invention provides for modifying the spatial orientation of one or more types of the microphase separated domains by providing, for example, a corrugated surface as a substrate for the release region. The domains of a microphase separated mixture of polymers in a thin film have been found to be guidable into arbitrary structures by applying on a surface with a prepatterned variation of surface energies such as a corrugated surface. For example, the orientation of lamellae has been altered by modifying the periodicity of the corrugation (See Tsori and Andelman, "Parallel and Perpendicular Lamellae on Corrugated Surfaces," *Macromolecules* 2003, 36, 8560-8566).

In another aspect, the present invention provides medical devices, including insertable and implantable devices, formed according to the above method. As stated above, in certain preferable embodiments, the polymeric composition of the release region of the medical devices of the present invention comprises a microphase separated block copolymer. In even more preferred embodiment, the composition comprises a diblock or triblock copolymer wherein blocks of a first polymer are present as spheres, cylinders, or lamellae within a continuous matrix of a second block.

In accordance with some particularly preferred embodiments, two or more types of microphase separated domains are provided by a block copolymer that comprises one or more low Tg blocks and one or more additional blocks, for example, one or more high Tg blocks or one or more biodisintegrable blocks. As specific examples, in some particularly preferred embodiments, the microphase separated domains are provided by a block copolymer comprising a low Tg polyisobutylene block and one or two high Tg polystyrene blocks.

A "low $T_g$ polymer block" is a polymer block that displays a glass transition temperature ($T_g$), as measured by any of a number of techniques including differential scanning calorimetry (DSC), dynamic mechanical analysis (DMA), or dielectric analysis (DEA), that is below ambient temperature, more typically below about 25° C., below about 0° C., below about −25° C., or even below about −80° C. "Ambient temperature" is typically 25° C.-45° C., more typically body temperature (e.g., 35° C.-40° C.). As a result of their low glass transition temperature, low $T_g$ polymer blocks are typically elastomeric at ambient temperature. Homopolymers of some low Tg polymer blocks, such as linear or branched silicone (e.g. polydimethylsiloxane), are viscous liquids or millable gums at room temperature and become elastomeric upon covalent cross-linking.

Specific examples of low $T_g$ polymer blocks from which low $T_g$ polymer blocks can be selected in accordance with the present invention include homopolymers and copolymer blocks formed from (or having the appearance of being formed from) the following: acrylic monomers, methacrylic monomers, vinyl ether monomers, cyclic ether monomers, ester monomers, unsaturated hydrocarbon monomers, including alkene monomers, halogenated alkene monomers, halogenated unsaturated hydrocarbon monomers, and siloxane monomers. Numerous specific examples are listed below. The $T_g$ values are published values for homopolymers of the listed monomeric unit.

Specific acrylic monomers include: (a) alkyl acrylates such as methyl acrylate ($T_g$ 10° C.), ethyl acrylate ($T_g$ −24° C.), propyl acrylate, isopropyl acrylate ($T_g$ −11° C., isotactic), butyl acrylate ($T_g$ −54° C.), sec-butyl acrylate ($T_g$ −26° C.), isobutyl acrylate ($T_g$ −24° C.), cyclohexyl acrylate ($T_g$ 19° C.), 2-ethylhexyl acrylate ($T_g$ −50° C.), dodecyl acrylate ($T_g$ −3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ −50° C.) and 2-methoxyethyl acrylate ($T_g$ −50° C.), (d) halo-alkyl acrylates such as 2,2,2-trifluoroethyl acrylate ($T_g$ −10° C.) and (e) cyano-alkyl acrylates such as 2-cyanoethyl acrylate ($T_g$ 4° C.).

Specific methacrylic monomers include (a) alkyl methacrylates such as butyl methacrylate ($T_g$ 20° C.), hexyl methacrylate ($T_g$ −5° C.), 2-ethylhexyl methacrylate ($T_g$ −10° C.), octyl methacrylate ($T_g$ −20° C.), dodecyl methacrylate ($T_g$ −65° C.), hexadecyl methacrylate ($T_g$ 15° C.) and octadecyl methacrylate ($T_g$ −100° C.) and (b) aminoalkyl methacrylates such as diethylaminoethyl methacrylate ($T_g$ 20° C.) and 2-tert-butyl-aminoethyl methacrylate ($T_g$ 33° C.).

Specific vinyl ether monomers include (a) alkyl vinyl ethers such as methyl vinyl ether ($T_g$ −31° C.), ethyl vinyl ether ($T_g$ −43° C.), propyl vinyl ether ($T_g$ −49° C.), butyl vinyl ether ($T_g$ −55° C.), isobutyl vinyl ether ($T_g$ −19° C.), 2-ethylhexyl vinyl ether ($T_g$ −66° C.) and dodecyl vinyl ether ($T_g$ −62° C.).

Specific cyclic ether monomers include tetrahydrofuran ($T_g$ −84° C.), trimethylene oxide ($T_g$ −78° C.), ethylene oxide ($T_g$ −66° C.), propylene oxide ($T_g$ −75° C.), methyl glycidyl ether ($T_g$ −62° C.), butyl glycidyl ether ($T_g$ −79° C.), allyl glycidyl ether ($T_g$ −78° C.), epibromohydrin ($T_g$ −14° C.), epichlorohydrin ($T_g$ −22° C.), 1,2-epoxybutane ($T_g$ −70° C.), 1,2-epoxyoctane ($T_g$ −67° C.) and 1,2-epoxydecane ($T_g$ −70° C.).

Specific ester monomers (other than acrylates and methacrylates) include ethylene malonate ($T_g$ −29° C.), vinyl acetate ($T_g$ 30° C.), and vinyl propionate ($T_g$ 10° C.).

Specific alkene monomers include ethylene, propylene ($T_g$ −8 to −13° C.), isobutylene ($T_g$ −73° C.), 1-butene ($T_g$ −24° C.), trans-butadiene ($T_g$ −58° C.), 4-methyl pentene ($T_g$ 29° C.), 1-octene ($T_g$ −63° C.) and other α-olefins, cis-isoprene ($T_g$ −63° C.), and trans-isoprene ($T_g$ −66° C.).

Specific halogenated alkene monomers include vinylidene chloride ($T_g$ −18° C.), vinylidene fluoride ($T_g$ −40° C.), cis-chlorobutadiene ($T_g$ −20° C.), and trans-chlorobutadiene ($T_g$ −40° C.).

Specific siloxane monomers include dimethylsiloxane ($T_g$ −127° C.), diethylsiloxane, methylethylsiloxane, methylphenylsiloxane ($T_g$ −86° C.), and diphenylsiloxane.

In certain preferred embodiments, the one or more low $T_g$ polymer blocks are biostable polymer blocks. A "biostable" polymer block is one that remains associated with the medical device during its period of residence within a patient. Typical examples of biostable low Tg polymer blocks include polyisobutylene blocks and polysiloxane blocks.

The low Tg polymer blocks may be present in the copolymer, for example, as interior blocks, as endblocks, as main chains, as side chains, and so forth. The low $T_g$ polymer blocks may be provided in copolymers having a variety of configurations, including cyclic, linear and branched configurations. Branched configurations include star-shaped configurations (e.g., configurations in which three or more chains emanate from a single chemical junction), graft copolymer configurations (e.g., configurations having a main chain (backbone) and a plurality of side chains connected to the backbone at multiple grafting points) and dendritic configurations (e.g., arborescent and hyperbranched blocks). The chain or chains forming low $T_g$ polymer blocks may contain, for example, a repeating series of constitutional units of a single type, or a series of constitutional units of two or more types, for instance, arranged in a repeating (e.g., alternating), random, statistical or gradient distribution.

In certain embodiments, the low $T_g$ polymer blocks are based upon homopolymers and copolymers of one or more elastomeric materials, such as polyalkylsiloxanes, polyolefins, polyacrylates or other polymers with a glass transition temperature at or below room temperature. For example, in certain embodiments, the blocks comprise polyolefinic blocks having alternating quaternary and secondary carbons of the general formulation: —(CRR'—CH$_2$)$_n$—, where R and R' are linear or branched aliphatic groups such as methyl, ethyl, propyl, isopropyl, butyl, isobutyl and so forth, or cyclic aliphatic groups such as cyclohexane, cyclopentane, and the like, with and without pendant groups. Preferred polyolefinic blocks include blocks of polymerized isobutylene, (i.e., polymers where R and R' are the same and are methyl groups).

In some other embodiments, polyolefin and polydiene blocks such as functionalized polyolefin and polydiene blocks (which are commercially available with functionalized end groups such as poLichelic™ polymers from FMC Lithium) are employed. In yet other embodiments, the low Tg polymer block comprises EPDM (ethylene-propylene-diene monomer) copolymer blocks (e.g., Vistalon™ polymers from Exxon-Mobil), which contain units formed from two olefins (ethylene and propylene) and one or more dienes (e.g., vinyl norbornene or ethylidene norbornene).

An elevated or "high Tg polymer block" is a polymer block that displays one or more glass transition temperatures, as measured by any of a number of techniques including differential scanning calorimetry, dynamic mechanical analysis, or thermomechanical analysis, which is above ambient temperature, more typically more typically above 50° C., above 60° C., above 70° C., above 80° C., above 90° C. or even above 100° C.

In some preferred embodiments, two or more types of microphase separated domains are provided by a block copolymer comprising one or more high Tg blocks and one or more additional blocks, for example, one or more biodisintegrable blocks and/or one or more low Tg blocks as discussed above. In some embodiments, the copolymer will have one or more glass transition temperatures below ambient temperature and one or more glass transition temperatures above ambient temperature, due to the presence of one or more low $T_g$ blocks and one or more high $T_g$ polymer blocks. This typically results in the formation of rubbery and hard phases within the release region at ambient temperatures.

As with the low Tg polymer blocks described above, the high Tg polymer blocks may be present in the copolymers, for example, as interior blocks, as endblocks, as main chains, as side chains, and so forth. Moreover, the high Tg polymer blocks may be provided in copolymers having a variety of configurations, including cyclic, linear and branched configurations. Branched configurations include star-shaped configurations (e.g., configurations in which three or more chains emanate from a single chemical junction point), graft copolymer configurations (e.g., configurations having a main chain backbone and a plurality of branching side chains emanating from multiple junction points) and dendritic configurations (e.g., arborescent and hyperbranched polymers). The high Tg polymer blocks may contain, for example, a repeating series of units of a single type, a series of units of two or more types in a repeating (e.g., alternating), random, statistical or gradient distribution, and so forth.

Specific examples of high $T_g$ polymer blocks from which high $T_g$ polymer blocks can be selected in accordance with the present invention include homopolymers and copolymer blocks formed from (or having the appearance of being formed from) the following: vinyl aromatic monomers, other vinyl monomers (besides vinyl aromatic monomers), other aromatic monomers (besides vinyl aromatic monomers), other methacrylic monomers (besides the above low Tg methacrylic monomers), other acrylic monomers (besides the above low Tg acrylic monomers), and other alkene monomers (besides the above low Tg alkene monomers).

Vinyl aromatic monomers are those having aromatic and vinyl moieties and include unsubstituted monomers, vinyl-substituted monomers and ring-substituted monomers. Specific vinyl aromatic monomers include the following: (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as =-methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Specific other vinyl monomers include the following: (a) vinyl alcohol ($T_g$ 85° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.), (d) vinyl halides such as vinyl chloride ($T_g$ 81° C.) and vinyl fluoride ($T_g$ 40° C.); (e) alkyl vinyl ethers such as methyl vinyl ether ($T_g$ -31° C.), propyl vinyl ether ($T_g$ -49° C.), butyl vinyl ether ($T_g$ -55° C.), isobutyl vinyl ether ($T_g$ -19° C.), tert-butyl vinyl ether ($T_g$ 88° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Specific other aromatic monomers, other than vinyl aromatics, include acenaphthalene ($T_g$ 214° C.) and indene ($T_g$ 85° C.).

Specific other methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Specific other acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as isopropyl acrylate ($T_g$ -11° C.), tert-butyl acrylate ($T_g$ 43-107° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.).

Specific other alkene based monomers include the following: ethylene (HDPE) ($T_g$ -125° C.), isotactic propylene ($T_g$ -8° C.), 4-methyl pentene ($T_g$ 29° C.), 1-octadecene ($T_g$ 55° C.), and tetrafluoroethylene ($T_g$ 117° C.).

One preferred group of block copolymers has (a) a low $T_g$ polymer midblock or main chain, including the examples listed above, for instance, polyisobutylene or polydimethylsiloxane and (b) one or more high $T_g$ endblocks or side chains, including the examples listed above, for instance, blocks of polystyrene or poly(alkyl methacrylate). In some specific embodiments the copolymer comprises (i) a low Tg block and (ii) a graft copolymer endblock, where the graft copolymer endblock comprises a main chain and a plurality of side chains. Block copolymers having more complex structures can also be employed in the practice of the present invention. For example, the release region may comprise a first phase comprising a low Tg polymer midblock such as polydimethylsiloxane or polyisobutylene and a second phase comprising a graft copolymer block comprising poly(alkylmethacrylate)-graft-polystyrene copolymer.

In certain preferred embodiments, block copolymers for use in conjunction with the present invention comprise blocks that are formed from a biodisintegrable material, i.e., a material that is subject to dissolution, biodegradation, resorption, etc., during its period of residence within a patient), such as one or more polyester blocks selected from a poly(glycolic acid) block, a poly(lactic acid) block, a poly(lactic acid-co-glycolic acid) block and a polycaprolactone block, or blocks comprising other biodisintegrable materials. For example, the copolymers may comprise one or more blocks comprising biodisintegrable materials such as those commercially available from Polymerix Corp. (Piscataway, N.J.) (e.g., bioerodable polyanhydrides), TyRx Pharma Inc. (New Brunswick, N.J.) (e.g., biodegradable tyrosine polyarylates) and Medi-Vas, LLC (San Diego, Calif.) (e.g., other amino acid based polyamides such as poly(ester amides)).

Further examples of homopolymers and copolymers for use in forming immiscible phases within the release regions of the present invention can be selected from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including. nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (crosslinked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Particularly preferred block copolymers include those described in U.S. Pat. No. 6,545,097 to Pinchuk et al., hereby incorporated by reference in its entirety. Specific examples of copolymers described therein include block copolymers of polyisobutylene and polystyrene, for example, polystyrene-polyisobutylene-polystyrene triblock copolymers (SIBS copolymers).

In certain preferred embodiments, the block copolymer comprises an ionomer. As used herein, ionomer refers to a polymer containing ionic groups, e.g., a copolymer having both nonionic repeating units and ion-containing repeating units such as sulphonated polystyrene blocks in a triblock copolymer comprising polystyrene-polyisobutylene-polystyrene.

Release regions for use in accordance with the present invention include carrier regions and barrier regions. By "carrier region" is meant a release region which further comprises a therapeutic agent and from which the therapeutic agent is released. For example, in some embodiments, a carrier region is disposed over all or a portion of a medical device, which acts as a substrate. In other embodiments, a carrier region constitutes the entirety of the medical device substrate. By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

In various embodiments, release regions for use in accordance with the present invention are in the form of release layers, which cover all or a part of a medical device substrate. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein. Release layer thicknesses for the practice of the present invention commonly range from about 1 to about 50 microns.

Numerous techniques are available for forming the polymeric release regions of the present invention. For example, where the one or more polymers have thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths. An electric and/or other orienting field (e.g., shear or solvent gradient) is applied during the transition of the polymeric release region from the melt stage into the solid stage, thereby affecting the spatial orientation of at least one of the types of microphase separated polymer domains with respect to the surface of the release region. The transition from melt to solid tends to "lock" the spatial orientation of the immiscible phases into place.

Using these and other techniques, entire devices or portions thereof can be made. For example, an entire stent can be extruded using the above techniques. As another example, a coating can be provided by extruding a coating layer onto a pre-existing stent. As yet another example, a coating can be co-extruded along with an underlying stent body.

If the therapeutic agent is stable at processing temperatures, then it can be combined with the one or more polymers prior to thermoplastic processing, producing a therapeutic-agent containing carrier region. If not, then a carrier region can nonetheless be formed by subsequent introduction of therapeutic agent, for example, as discussed below.

Polymeric release regions can also be formed in accordance with the present invention using solvent-based techniques in which one or more polymers (and optionally, a therapeutic agent) are first dissolved or dispersed in a solvent system and the resulting mixture subsequently used to form the polymeric release region. An electric and/or other orienting field (shear or solvent gradient) is applied as solvent is removed, thereby affecting the spatial orientation of at least one of the immiscible phases with respect to the surface of the release region. Removal of the solvent tends to "lock" the spatial orientation of the immiscible phases into place.

Where solvent-based techniques are used, the solvent system that is selected will contain one or more solvent species.

The solvent system is typically a good solvent for the one or more polymers and, where included, for the therapeutic agent. The particular solvent species that make up the solvent system may also be selected based on other characteristics including drying rate and surface tension.

Beneficial solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In various embodiments, a mixture containing solvent, one or more polymers and optional therapeutic agent, is applied to a substrate to form a release region. For example, the substrate can be all or a portion of an implantable or insertable medical device, such as a stent, to which a release layer is applied. On the other hand, the substrate can also be, for example, a template from which the polymeric release region is removed after solvent elimination. Such template-based techniques are particularly appropriate for forming simple objects such as sheets, tubes, cylinders and so forth, which can be easily removed from a template substrate.

Where appropriate, techniques such as those listed above can be repeated or combined to build up a release layer to a desired thickness. The thickness of the release layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be dissolved or dispersed in the polymer/solvent mixture if desired, and hence co-established with the carrier region. In other embodiments, the therapeutic agent can be dissolved or dispersed within a solvent, and the resulting solution contacted with a polymer region that is previously formed using, for example, one or more of the techniques described herein.

Barrier layers, on the other hand, are formed over a therapeutic-agent-containing region. For example, a barrier layer can be formed over a therapeutic-agent-containing region using solvent-based techniques such as those discussed above in which the one or more polymers are first dissolved or dispersed in a solvent, and the resulting mixture is subsequently used to form the barrier layer. The barrier layer serves, for example, as a boundary layer to retard diffusion of the therapeutic agent, for example, acting to prevent a burst phenomenon whereby much of the therapeutic agent is released immediately upon exposure of the device or a portion of the device to the implant or insertion site. As would be appreciated by one of skill in the art, the barrier layer may also be exposed to electric field alignment or other orienting field to alter its morphology. For example, the barrier layer may be oriented such that its alignment is substantially perpendicular to that which is generated for enhanced drug delivery or that of an adjoining therapeutic-agent-containing region to provide improved barrier function.

In some embodiments, the therapeutic-agent-containing region beneath the barrier region will comprise one or more polymers such as those described elsewhere herein. The polymeric composition of the barrier region may, or may not be the same as the polymeric composition of the underlying therapeutic-agent-containing region. As such, the therapeutic-agent-containing region can also be established using techniques such as those discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be contacted with a substrate again using, for instance, one or more of the above-described application techniques.

In some embodiments, an overall desired release profile of a therapeutic agent may be achieved by employing a plurality of release regions in accordance with the present invention, including a plurality of carrier regions, a plurality of barrier regions, or a combination of carrier and barrier regions, which collectively provide an overall desired release profile of a therapeutic agent from the medical device of the present invention. For example, in some embodiments, the release regions comprise a plurality of layers which form a conformal coating on a medical device substrate, wherein at least one of the layers comprises a barrier region, and at least one of the layers comprises a carrier region. These layers may alternate between carrier and barrier regions. In other embodiments, one or more barrier regions may overlap portions of one or more carrier regions and vice versa. For example, a single barrier region may be disposed over a plurality of discrete carrier regions, or a plurality of barrier regions may be disposed over a single carrier region. Any such variations in the thickness, number, order or position of the carrier and barrier regions with respect to one another are within the scope of the present invention.

As will be appreciated by one of skill in the art, the copolymers of the present invention may be synthesized according to known methods, including cationic, anionic and radical polymerization methods, such as azobis(isobutyronitrile)- or peroxide-initiated processes and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes. These methods are well-detailed in the literature and are described, for example, in an article by Pyun and Matyjaszewski, "Synthesis of Nanocomposite Organic/Inorganic Hybrid Materials Using Controlled/ "Living" Radical Polymerization," *Chem. Mater.*, 13:3436-3448 (2001), the contents of which are incorporated by reference in its entirety.

Medical devices for use in conjunction with the present invention include essentially any medical device for which controlled release of a therapeutic agent is desired. Examples of medical devices include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and tissue engineering scaffolds for cartilage, bone, skin and other in vivo tissue regeneration.

The medical devices of the present invention include medical devices that are used for either systemic treatment or for the localized treatment of any mammalian tissue or organ. As used herein, "treatment" refers to the prevention of a disease or condition, the reduction or elimination of symptoms associated with a disease or condition, or the substantial or complete elimination of a disease or condition. Preferred subjects are mammalian subjects and more preferably human subjects. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, vagina, uterus, ovary, and prostate; skeletal muscle; smooth muscle; breast; dermal tissue; cartilage; and bone.

Specific examples of medical devices for use in conjunction with the present invention include vascular stents, which deliver therapeutic agent into the vasculature for the treatment of restenosis. In these embodiments, the release region is typically provided over all or a portion of a stent substrate, and is typically in the form of one or more carrier layers (in which case therapeutic agent is disposed within the release layer) or one or more barrier layers (in which case the release layer is disposed over a therapeutic-agent containing region).

Therapeutic agents may be used singly or in combination in the medical devices of the present invention. "Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-contairiing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; and (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomycin D, Resten-NG, Ap-17, abciximab, clopidogrel and Ridogrel, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor $\alpha$ and $\beta$, platelet-derived endothelial growth factor, platelet-derived growth factor, tumor necrosis factor $\alpha$, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Therapeutic agents also include ablation agents, sufficient amounts of which will result in necrosis (death) of undesirable tissue, such as malignant tissue, prostatic tissue, and so forth. Examples include osmotic-stress-generating agents, for example, salts such as sodium chloride or potassium chloride; organic solvents, particularly those such as ethanol, which are toxic in high concentrations, while being well tolerated at lower concentrations; free-radical generating agents, for example, hydrogen peroxide, potassium peroxide or other agents that can form free radicals in tissue; basic agents such as sodium hydroxide; acidic agents such as acetic acid and formic acid; enzymes such as collagenase, hyaluronidase, pronase, and papain; oxidizing agents, such as sodium hypochlorite, hydrogen peroxide or potassium peroxide; tissue fixing agents, such as formaldehyde, acetaldehyde or glutaraldehyde; and naturally occurring coagulants, such as gengpin.

A wide range of therapeutic agent loadings can be used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

EXAMPLE

1. Preparation of SIBS Film

Films of polystyrene-polyisobutylene-polystyrene (SIBS) triblock copolymer of different thicknesses were prepared by spin casting in toluene. A 29% (w/v) polymer solution in toluene was spun cast at 1000 rpm on a substrate comprising a $SiO_2$/silicon wafer (100 plane growth, of 475-575 microns, commercially available from International Wafer Service, Inc., Colfax, Calif.) to produce a film having a thickness of about 600 nm to about 800 nm. The film thickness was controlled by adjusting solution concentrations and spin cast rates and film thickness was measured using standard techniques including ellipsometry, dektak profilemeter, filmetrics or atomic force microscopy (AFM). Films thicker than about 5 microns were made using a Stanat Two-Roll Calendar operated at 160° C. Films having a thickness of about 2.6 microns were prepared by spin casting from a 10% (w/v) solution in toluene at 500 rpm. The films were spin cast longer than about 40 seconds in order to reduce the amount of residual solvent remaining on the film.

2. Electric Field Alignment of SIBS Film

Figure 2:
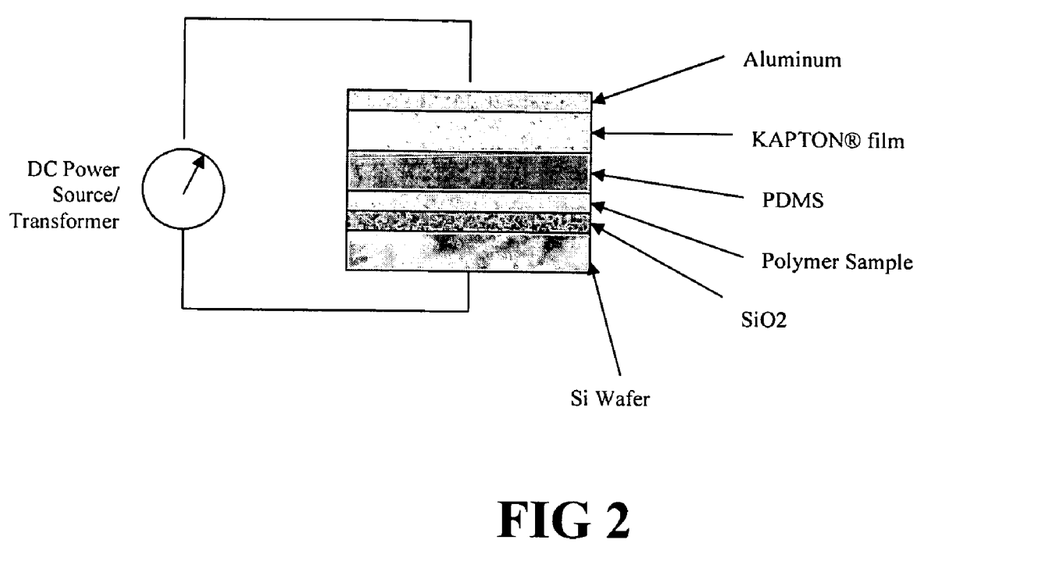
FIG. 2 schematically illustrates an electrode/film assembly for electric field alignment of a polymer film.

An electrode/polymer assembly comprising SIBS film between a top and bottom electrode was assembled as shown in FIG. 2. Although any conductive material may be used for both the top and bottom electrodes, aluminized KAPTON® (e.g., a polyimide coated with aluminum, DuPont High Performance Materials, Circleville, Ohio) having a thickness of about 1.0 mil (25.4 µm) was used as the top electrode. The bottom electrode comprised the SIBS coated silicon wafer substrate prepared above. As shown in FIG. 2, a thermally grown $SiO_2$ layer was about 2 nm. For relatively thick films (about 10 microns or higher), the SIBS copolymer film is placed between the two electrodes. For thinner films, the surface roughness of the top electrode causes air pockets on the electrode surface. Thus, a thin layer of crosslinked PDMS (polydimethylsiloxane) was coated on top of the aluminized KAPTON® to produce a smooth surface.

The crosslinked PDMS, a two component mixture, is commercially available from The Dow Chemical Company, Midland, Mich. under the trademark SYLGARD 184®. Components A and B were mixed with a weight ratio of 10:1 as instructed by the vendor. The mixture was spun cast on top of the KAPTON® coated silicon wafer at a spin speed of about 300 rpm for about 30 seconds then slowly increased to 300 rpm for an additional 5 minutes, producing a thin film of about 15 to about 20 microns. The coated wafer was left overnight at room temperature to allow for some solvent evaporation. The KAPTON® was then cured at 60° C. under air atmosphere for 24 hours. The crosslinked PDMS films were further annealed at the electric field alignment temperature of 130° C. under vacuum for an additional 24 hours to remove any residual solvent. This procedure has also been shown to help reduce the diffusion of PDMS.

The assembly containing the film and the electrodes was annealed at 130° C. for 16 to 24 hours in a nitrogen gas atmosphere under an electric field strength of about 30 to 40V/micron. Based on the thickness of the sample, the crosslinked PDMS and aluminized PDMS, the applied voltage was typically about 1600 to 2000 VDC. While continuing to apply the electric field, the sample was then cooled down to room temperature to freeze the structure. Typically, the operating temperature should be above the glass transition temperature of all of the blocks of the copolymer, below its Order-Disorder-Transition temperature (ODT), and also comfortably below its thermal degradation temperature. As polystyrene and polyisobutylene are incompatible, coexisting phases and microphases of the almost pure copolymer components are found after film preparation. The domain morphology that forms during solvent evaporation was observed using atomic force microscopy and cross-sectional TEM, or SAXS. Specifically the 2.6 micron sample was left under the electric field at 130° C. for 24 hours at 1800 VDC resulting in an electric field strength of about 37V/micron. The power supply comprised a standard high voltage and low current device.

3. Characterization of SIBS Film

Figure 3:
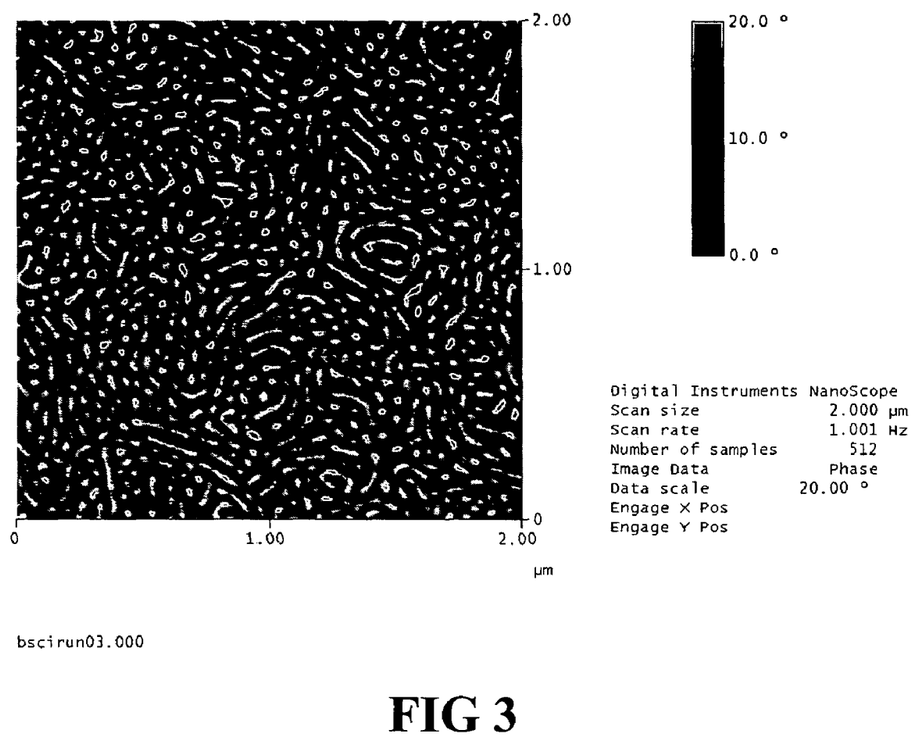
FIG. 3 are atomic force microscopy images showing the disordered surface topography of a polystyrene-polyisobutylene-polystyrene block copolymer film which was spun-cast from a toluene solution with no application of an external energy field ($E_o=0$).
Figure 4:
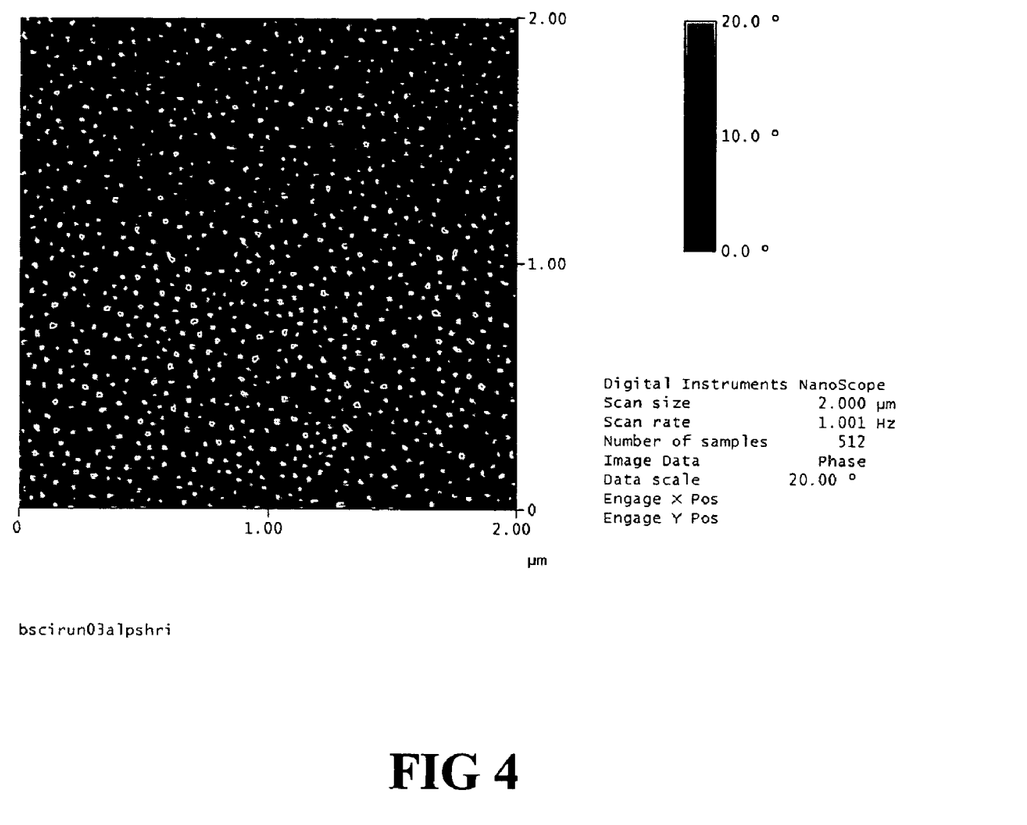
FIG. 4 are atomic force microscopy images showing the ordered surface topography of a polystyrene-polyisobutylene-polystyrene block copolymer film which was spun-cast from a toluene solution with the application of an external energy field application of $E_o=30\text{-}40\text{V/micron}$.

Atomic force microscopy was used to study the surface morphology in tapping mode of the SIBS films described above. FIG. 3 provides AFM phase images of the SIBS block copolymer without the application of an external energy field (Eo=0). The topography image of the SIBS sample as spun cast exhibits a material contrast between the polystyrene domains and the polyisobutylene domains at the surface. Lighter regions are polystyrene and darker regions are the polyisobutylene matrix. As shown in FIG. 4, the AFM topography of a SIBS film formed while subjected to an electric field (Eo=30-40V/micron) is markedly different. Circular domains evenly spaced within a contrasting surrounding matrix indicate highly ordered alignment of the polystyrene and the polyisobutylene domains to produce a well-ordered cylindrical morphology of polystyrene within a surrounding polymer matrix of isobutylene.

Figure 5A:
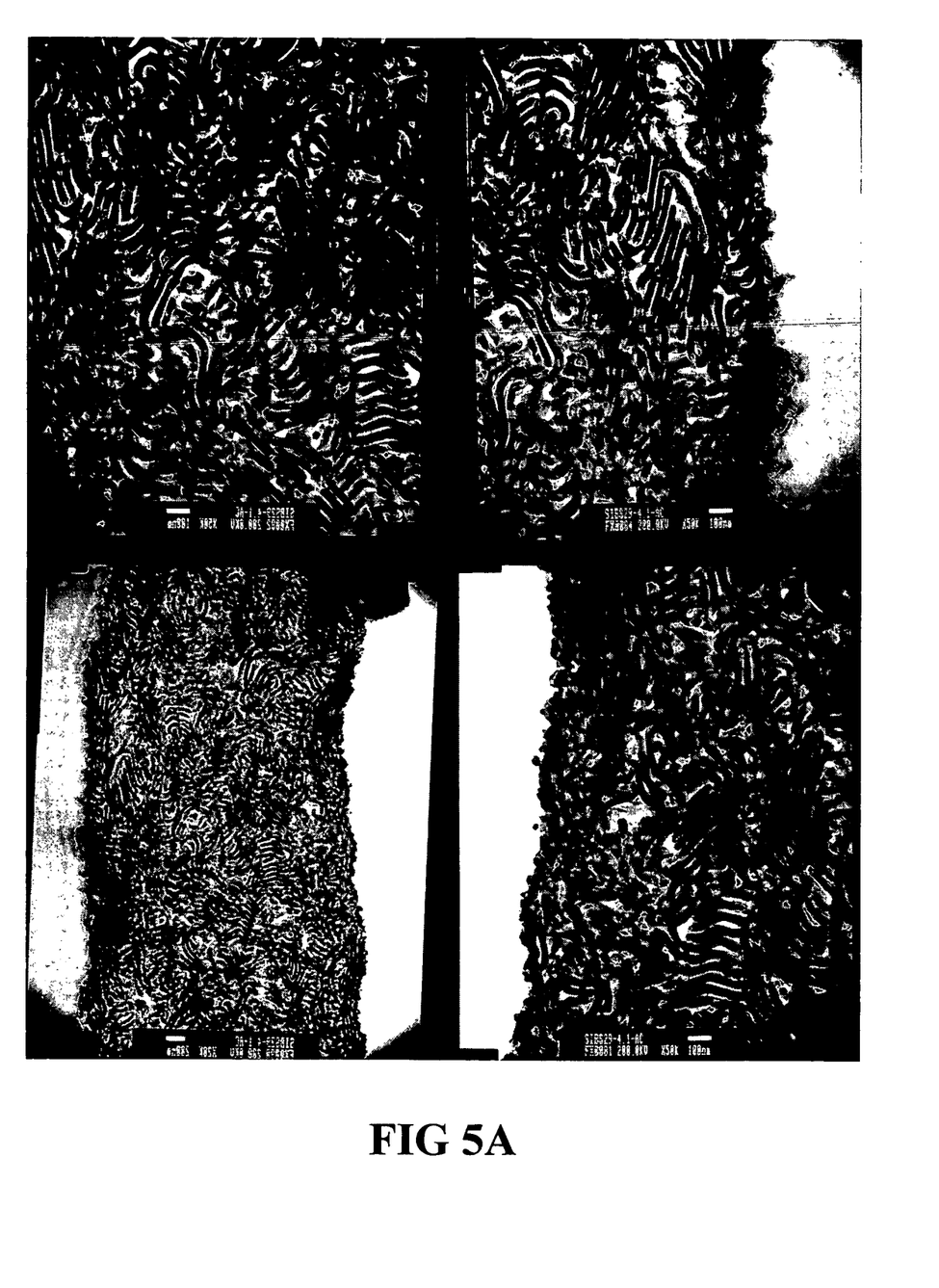
FIG. 5A are TEM images of a cross-section of a spun-cast polystyrene-polyisobutylene-polystyrene block copolymer film with no application of an external energy field (Eo=0) showing disordered cylindrical domains within a surrounding matrix.
Figure 5B:
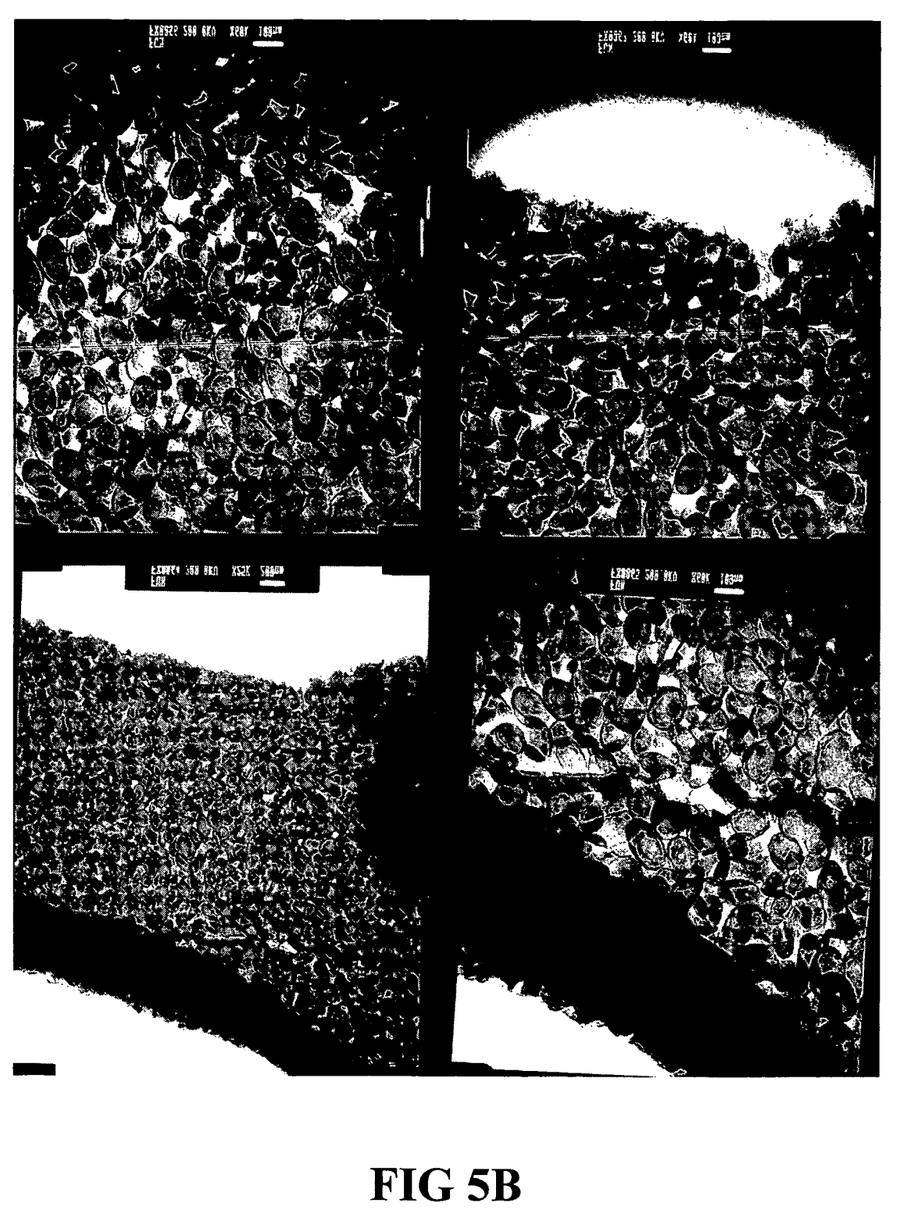
FIG. 5B are TEM images of a cross-section of a spun-cast polystyrene-polyisobutylene-polystyrene block copolymer film that has been aligned by the application of an external energy field (Eo=0) to form well-ordered cylindrical domains within a surrounding matrix that are aligned perpendicularly to the sample surface.

FIG. 5A shows several cross-sectional transmission electron microscopy (TEM) images of a SIBS block copolymer that has been spun cast as described above but which have not been subjected to an electric field (Eo=0). As shown in FIG. 5A, the morphology comprises a disordered plurality of cylindrical "noodle-like" structures within a surrounding matrix. FIG. 5A also shows several cross-sectional transmission electron microscopy (TEM) images of a SIBS block copolymer that has been spun cast and which have been subjected to an electric field according to the procedure described above (Eo=30-40V/micron). The images of FIG. 5B show that the cylinders are highly oriented when ordered under an electric field in contrast to Eo=0. A well-aligned set of circular cross-sections evidencing cylinders oriented perpendicular to the cross-sectional sample surface and parallel to the electric field can be seen.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of forming a medical device that comprises a therapeutic agent and a release region that regulates the rate at which the therapeutic agent is released from the medical device release, said method comprising:
   (a) providing a precursor region that comprises a polymer composition comprising a block copolymer comprising a high Tg block and a low Tg block, said polymer composition comprising two or more microphase separated polymer domains that are immiscible with one another; and
   (b) applying an orienting field comprising an electric field to said precursor region, wherein said electric field changes the spatial orientation of the microphase separated polymer domains within the precursor region, thereby forming said release region, and wherein said electric field is applied at a temperature that is above the glass transition temperature of all of the blocks of the copolymer;
   wherein said precursor region is formed before applying said orienting field.

2. The method of claim 1, wherein said release region comprises a release layer disposed over a substrate.

3. The method of claim 2, wherein said release layer is a carrier layer comprising said therapeutic agent.

4. The method of claim 2, wherein said release layer is a barrier layer disposed over a region that comprises said therapeutic agent.

5. The method of claim 2, wherein said release layer has a thickness ranging between about 1 and about 50 microns.

6. The method of claim 1, wherein said release region comprises a first microphase separated polymer domain that comprises a plurality of substantially aligned discontinuous cylinders within a second microphase separated polymer domain comprising a continuous polymer matrix.

7. The method of claim 1, wherein said microphase separated polymer domains comprise a plurality of alternating immiscible microphase separated lamellae.

8. The method of claim 6 or 7, wherein said cylinders or lamellae are aligned substantially parallel with a surface of said release region.

9. The method of claim 6 or 7, wherein said cylinders or lamellae are aligned substantially perpendicular with respect to a surface of said release region.

10. The method of claim 6 or 7, wherein said cylinders or lamellae are aligned substantially oblique with respect to a surface of said release region.

11. The method of claim 1, wherein said polymer composition comprises two or more polymers.

12. The method of claim 1, wherein said polymer composition comprises a mixture of two or more polymers selected from the following polymers: a polymer comprising an acrylic monomer, a polymer comprising a methacrylic monomer, a polymer comprising a vinyl ether monomer, a polymer comprising a vinyl aromatic monomer, a polymer comprising a vinyl alcohol monomer, a polymer comprising a vinyl ester monomer, a polymer comprising a vinyl amine monomer, a polymer comprising a vinyl halide monomer, a polymer comprising a cyclic ether monomer, a polymer comprising an ester monomer, a polymer comprising an unsaturated hydrocarbon monomer, and a polymer comprising a siloxane monomer.

13. The method of claim 1, wherein said polymer composition comprises an admixture of a polystyrene homopolymer and isobutylene homopolymer.

14. The method of claim 1, wherein said block copolymer comprises a first block that corresponds to a microphase separated domain comprising a plurality of discontinuous cylinders within a second block corresponding to a continuous polymer matrix.

15. The method of claim 1, wherein said block copolymer comprises a first block that corresponds to a first microphase separated domain comprising a plurality of lamellar layers and a second block corresponds to a second microphase separated domain comprising a second group of lamellar layers wherein the lamellar layers of the first and second domains form alternating immiscible lamellae.

16. The method of claim 1, wherein said block copolymer is a biostable block copolymer.

17. The method of claim 1, wherein said block copolymer comprises a biodisintegrable block.

18. The method of claim 1, wherein said block copolymer comprises two or more of the following blocks: a block comprising an acrylic monomer, a block comprising a methacrylic monomer, a block comprising a vinyl ether monomer, a block comprising a vinyl aromatic monomer, a block comprising a vinyl alcohol monomer, a block comprising a vinyl ester monomer, a block comprising a vinyl amine monomer, a block comprising a vinyl halide monomer, a block comprising a cyclic ether monomer, a block comprising an ester monomer, a block comprising an unsaturated hydrocarbon monomer, and a block comprising a siloxane monomer.

19. The method of claim 1, wherein said block copolymer comprises a polystyrene block and a polyisobutylene block.

20. The method of claim 1, wherein block copolymer is a polystyrene-polyisobutylene-polystyrene triblock copolymer.

21. The method of claim 1, wherein said block copolymer comprises (i) a low Tg block and (ii) a graft copolymer endblock, said graft copolymer endblock comprising a main chain and a plurality of side chains.

22. The method of claim 1, wherein said precursor region comprises a melt phase, and wherein said precursor region is subjected to said orienting field or combination of fields concurrently with the transition of said melt phase to a solid phase, thereby forming said release region.

23. The method of claim 1, wherein the strength of said electric field ranges from about 2 to about 50 V/micron.

24. A medical device formed according to the method of claim 1.

25. A method of forming a medical device that comprises a therapeutic agent and a release region that regulates the rate at which the therapeutic agent is released from the medical device release, said method comprising: (a) forming a precursor region from a solution that comprises (i) a solvent system and (ii) a block copolymer comprising two or more microphase separated domains which are immiscible with one another, and (iii) optionally, said therapeutic agent; and (b) applying an orienting field comprising an electric field to said precursor region while concurrently removing said solvent system from said solution, wherein said electric field is of sufficient strength to change the spatial orientation of the microphase separated domains within the precursor region to form said release region; wherein said precursor region is formed before applying said orienting field.

26. A medical device formed according to the method of claim 25.

27. The method of claim 1, wherein said block copolymer comprises a low Tg block displaying a glass transition temperature below 0° C. and a high Tg block displaying a glass transition temperature above 70° C.

28. The method of claim 27, wherein said electric field is applied at a temperature that is below the Order-Disorder-Transition Temperature (ODT) of the copolymer.

29. The method of claim 27, wherein the strength of said electric field ranges from about 2 to about 50 V/micron.

30. The method of claim 27, wherein said release region comprises a first microphase separated polymer domain that comprises a plurality of substantially aligned discontinuous cylinders within a second microphase separated polymer domain comprising a continuous polymer matrix, wherein said cylinders are aligned substantially perpendicular with respect to a surface of said release region.

31. The method of claim 27, wherein said microphase separated polymer domains comprise a plurality of alternating immiscible microphase separated lamellae, wherein said lamellae are aligned substantially perpendicular with respect to a surface of said release region.

32. The method of claim 25, wherein said release region is formed using a method selected from the group consisting of solvent casting techniques, spin coating techniques, web coating techniques, solvent spraying techniques and dipping techniques.

33. The method of claim 25, wherein said release region comprises a release layer disposed over a substrate.

* * * * *

UNITED STATES PATENT AND TRADEMARK OFFICE
CERTIFICATE OF CORRECTION

| | |
|---|---|
| PATENT NO. | : 7,964,209 B2 |
| APPLICATION NO. | : 11/005852 |
| DATED | : June 21, 2011 |
| INVENTOR(S) | : Shrirang V. Ranade |

Page 1 of 1

It is certified that error appears in the above-identified patent and that said Letters Patent is hereby corrected as shown below:

Col. 9, line 19-20, after "as" change "=" to --$\alpha$--.

Col. 19, line 34, after "to" change "300" to --3000--.

Signed and Sealed this
Twentieth Day of September, 2011

David J. Kappos
*Director of the United States Patent and Trademark Office*